United States Patent [19]

Sulc et al.

[11] Patent Number: 5,002,570
[45] Date of Patent: Mar. 26, 1991

[54] INTRAOCULAR HYDROGEL LENS WITH SHAPE MEMORY

[75] Inventors: Jiri Sulc; Zuzana Krcova, both of Prague, Czechoslovakia

[73] Assignee: Ceskoslovenska akademie ved, Prague, Czechoslovakia

[21] Appl. No.: 447,159

[22] Filed: Dec. 7, 1989

[51] Int. Cl.$^5$ .............................. A61F 2/16
[52] U.S. Cl. ............................................ 623/6
[58] Field of Search ................................. 623/6

[56] References Cited

U.S. PATENT DOCUMENTS

| | | | |
|---|---|---|---|
| 4,556,998 | 12/1985 | Sieper | 623/6 |
| 4,731,078 | 3/1988 | Stoy et al. | 623/6 |
| 4,731,079 | 3/1988 | Stoy | 623/6 |
| 4,831,954 | 3/1989 | Siepser | 623/6 |

FOREIGN PATENT DOCUMENTS 3800529  7/1988  Fed. Rep. of Germany .......... 623/6

Primary Examiner—Ronald Frinks
Attorney, Agent, or Firm—Leydig, Voit & Mayer

[57] ABSTRACT

An intraocular hydrogel lens with shape memory swelling in water or in isotonic solution, as is physiologic saline, which is deformed before implantation into a shape suitable for operative insertion, for example, into the shape of a rod, is made, at least in part, from a cross-linked synthetic hydrogel containing acid and/or basic groups.

5 Claims, No Drawings

INTRAOCULAR HYDROGEL LENS WITH SHAPE MEMORY

FIELD AND BACKGROUND OF THE INVENTION

The invention pertains to an intraocular hydrogel lens with shape memory swelling in water or isotonic solution, as is physiological saline, which is deformed before implantation to the shape suitable for operative introduction, for example to the shape of a rod, and is designated for insertion inside an eye into the anterior or posterior chamber or behind the cornea.

The intraocular lenses known so far are predominantly in a definite shape and physical state before their operative insertion into the eye. Such lenses are made either from hard polymers, as are polymers of esters of methacrylic acid or acrylic acid with lower aliphatic alcohols, for example, from methyl methacrylate (MMA), or from soft hydrogels swollen to equilibrium in physiological saline before insertion into the eye. A relatively long incision is needed in both cases in order to slide the lens into its place. The hard lenses cannot be deformed at applicable temperature to facilitate the insertion. With common hydrogel lenses from lightly crosslinked polymers, as is the polymer of hydroxyethyl methacrylate (HEMA), the possible temporary deformation is limited, if not excluded, by their elasticity and tendency to break at too sharp bending. Moreover, the hard lenses increase the risk of injury of sensitive eye tissues during insertion.

Recently an intraocular lens is known which is deformed before and during operation to a shape suitable for operative insertion, thus enabling one to shorten the incision (U.S. Pat. No. 4,731,079; Czechoslovak Patent Application No. 9596-86). The lens acquires its final shape first in the eye on the place designated for it.

The purposeful deformation is, for example, winding or compression of the lens to a narrow rod or, at least, its folding or coiling in order to reduce the necessary length of incision at least in half.

After operative insertion, which is considerably facilitated by this deformation, the lens relaxes in the eye under heating to eye temperature and thus acquires the desirable original shape, elasticity, and softness. The rate of unfolding is given beforehand and the surgeon has to work very quickly and with handiness without making a mistake.

According to the references mentioned above, the lens is either not swollen to equilibrium and undergoes postswelling in eye (Czechoslovak Patent Application No. 9596-86) or is swollen to equilibrium with a low content of water (up to 20%) and the water content does not change in eye (U.S. Pat. No. 4,731,079).

SUMMARY OF THE INVENTION

This invention provides an intraocular lens with shape memory in water or in isotonic solution, as is physiologic saline, which is deformed before implantation into a shape suitable for operative insertion (for example, according to Czechoslovak Patent Application No. 9596-86), and made from a at least in part cross-linked synthetic hydrogel containing acid and/or basic groups.

DETAILED DESCRIPTION OF THE INVENTION

The acid and/or basic groups may be present in the whole mass of the lens or in the surface layer of the lens 1 to 200 μm thick or only in some other part of lens. This depends on the required application (the rate of decoiling, secondary deformation).

The acid groups, which are used according to the invention, are present, for example, in sulfoalkyl (meth)acrylate, sulfoalkyl(meth)acrylamide, (meth)acrylic acid, and other such compounds.

The basic groups, which are used according to the invention, are present, for example, in aminoalkyl (meth)acrylate, aminoalkyl(meth)acrylamide, vinylpyridine, their quaternary ammonium salts, and other such compounds.

In the production of intraocular lenses the following may be used: copolymers which contain acid and/or basic groups in the form of acids and bases (for example, the copolymers of 2-hydroxyethyl methacrylate—methyl methacrylate—(meth)acrylic acid, 2-hydroxyethyl methacrylate—(meth)acrylic acid, and others) or copolymers which contain these acid or basic groups in the form of salts and are additionally transferred into the acid or basic form by changing pH (for example, the copolymers of 2-hydroxyethyl methacrylate—sodium or potassium (meth)acrylate, 2-hydroxyethyl methacrylate—methyl methacrylate—sodium or potassium (meth)acrylate).

The acid or basic groups may be also created by a polymeranalogous reaction of some polymers, for example, by acid or alkaline hydrolysis.

It makes no difference in this case whether only acid groups or only basic groups are present in the polymer or whether both acid and basic groups are present at the same time.

The lens according to this invention utilizes the changing water content in hydrogel depending on the pH and ionic strength of the medium. The hydrogels containing acid and/or basic groups change their water content depending upon the on ionic strength and pH of the medium (according to pK of the acid or base). This phenomenon is caused by the degree of dissociation of acid or basic groups. For example, the dissociation constant of methacrylic acid is 5.1, which means that the swelling of hydrogel containing this and steeply rises if pH is above 5.

Because ionic strength of body liquids is constant and pH ranges between 7.0 and 7.2, copolymers may be prepared which are elastic under these conditions and become tough at lower (acids) or higher (basic) values of pH. In particular, cross-linked copolymers and terpolymers of acrylic acid or methacrylic acid with methyl methacrylate or 2-hydroxyethyl methacrylate are relevant. After heating such a polymer above $T_g$, deformation, and cooling, the polymer remains in the deformed state until ionic strength or pH of the surrounding medium is changed.

The equilibrium swelling of the lens according to the invention is lower in the acid or basic cycle than the equilibrium swelling after neutralization of acid or basic groups.

The more ionogenic groups in the polymer, the higher is the difference between equilibrium swelling in the acid or basic form and the equilibrium swelling in the neutralized form.

It is possible to use the replaced by the ionic strength and pH dependent swelling capacity of the lenses to obtain lenses which after implantation are unfolded and afterwards swell and soften.

It is possible to use the increased swelling capacity of the lenses in salt form in water in comparison with the physiologic saline solution. Such lenses after implantation unfold, deswell and harden.

Also a doubled successive deformation can be obtained with the intraocular lens with shape memory according to the invention, which depends on pH and ionic strength. It is started with a lens, the acid or basic groups of which are transferred into the form of salt. Then a part of the lens, advantageously its rear side, i.e. the side which is turned to the inside of the eye after implantation, is transferred into the acid or basic cycle, whereas the other part of lens remains in the form of salt. This can be achieved by local action of solutions of strong acids or bases or by their electrolytic formation.

The content of water is adapted and the lens is then deformed and cooled (for example, according to Czechoslovak Patent Application No. 9596-86). After insertion of this deformed lens into eye, the lens is decoiled by the effect of temperature, but is bent due to uneven swelling of its parts (the lower part swells less, the upper part more) in such a way that it can be easily slid through the pupil into posterior chamber where the part occurring in the acid or basic cycle (i.e. the lower part in the given case) is again transferred into the form of salt (as it is with the other part of lens) due to the buffer capacity of body liquids.

Various deformations can be obtained in this way with the lens according to the invention which follow from the different swelling in the acid or basic form versus the neutralized form.

Any suitable method can be used for shaping the intraocular lens according to the invention, for example, rotation casting with polymerization or copolymerization and/or crosslinking carried out at the same time, or turning from a xerogel, or pressing, or injection moulding, and other methods.

The non-crosslinked lenses may be additionally crosslinked, for example, by radiation or an additional introduction of a crosslinking agent and heating in the presence or absence of a suitable polymerization initiator. For shaping by injection moulding there may be used also solutions of the pertinent polymer in a suitable solvent miscible with water, which is removed by washing. The deformed lens after operative insertion into the eye postswells and relaxes soon, e.g. within several seconds to minutes, by the change of pH. The lens acquires by relaxation its original shape, elasticity, and softness.

The invention is further illustrated in an example of real performance.

Example

A mixture of 35 wt. $-\%$ methyl methacrylate, 60 wt. $-\%$ 2-hydroxyethyl methacrylate, and 5 wt. $-\%$ methacrylic acid containing 0.05% diisopropyl peroxocarbonate was charged into an ampoule. The mixture was then bubbled through with argon and the ampoule was sealed and heated to 40° C. for 12 hours, to 60° C. for 24 hours, and to 80° C. for 24 hours. The ampoule was broken and a polymeric plug was removed. An intraocular lens was turned from the plug, polished, and allowed to swell in an isotonic solution of $NaHCO_3$. The equilibrium swelling of the lens amounted to 24 wt. $-\%$. The lens was washed in physiologic saline, pressed in the swollen state by its lower face to the filtration paper soaked with 1N HCl solution, and allowed in this position for 5 minutes. Then it was again washed with physiologic saline. The lens deswelled in the place of contact and bent. In this state it was sterilized in an autoclave. Before implantation it was heated to 50° C. and deformed using deformation equipment to the shape of a rod, cooled to 15° C., and inserted through a 3.5—mm incision into the anterior chamber of an eye. The lens decoiled there within about 30 seconds, but its supporting parts remained bent so that the lens could be easily slid through the pupil into posterior chamber of the eye, where it stepwise turned straight under the effect of stable pH of chamber liquid. This process lasted about 5–8 minutes.

We claim:

1. An intraocular lens shape memory swelling in water or isotonic solution, as which is deformed before implantation into a shape suitable for operative insertion wherein the lens is made, at least in part, from a crosslinked synthetic hydrogel comprising one or more swellable or deswellable regions containing acid groups, basic groups, or both, said lens being (1) either swellable or deswellable upon insertion into an eye and (2) reformable into a shape suitable as an intraocular lens, upon implantation into an eye, said lens being at least partially swellable upon implantation when it comprises a swellable region containing said acid groups, basic groups, or both, present as free acid or basic groups, or both, and said lens being at least partially deswellable upon implantation when it comprises a deswellable region containing said acid groups, basic groups, or both present in a salt form the swellable regions having a higher hydration capacity in isotonic solutions than in water and the deswellable regions having a lower hydration capacity in isotonic solutions than in water.

2. The intraocular lens according to claim 1, wherein the acid groups, basic groups, or both are in the surface layer of the lens, 1 to 200 mm. thick.

3. The intraocular lens according to claim 1, wherein the acid and/or basic groups are or the lower part of the lens which is, after implantation, capable of being turned inward of the eye.

4. The intraocular hydrogel lens according to claim 1, wherein the lens after implantation deswells and hardens.

5. The lens of claim 1 wherein the lens has (1) a swellable surface region comprised of free acid groups, free base groups, or both, said swellable region having a higher hydration capacity in isotonic solutions than in water, and (2) a deswellable surface region comprised of acid groups, base groups, or both, which groups are present in a salt form, said deswellable surface region having a lower hydration capacity in isotonic solutions than in water.

* * * * *